(12) United States Patent
Denys et al.

(10) Patent No.: US 10,537,643 B2
(45) Date of Patent: Jan. 21, 2020

(54) CHEMOEMBOLIZATION COMPOSITION COMPRISING ANTI-ANGIOGENIC AGENTS

(71) Applicant: CENTRE HOSPITALIER UNIVERSITAIRE VAUDOIS, Lausanne (CH)

(72) Inventors: Alban Denys, Lausanne (CH); Pierre Bize, Cheseaux (CH); Olivier Jordan, Prangins (CH); Eric Doelker, Conches (CH); Nathalie Boulens, Confignon (CH)

(73) Assignee: CENTRE HOSPITALIER UNIVERSITAIRE VAUDOIS, Lausanne (CH)

( * ) Notice: Subject to any disclaimer, the term of this patent is extended or adjusted under 35 U.S.C. 154(b) by 147 days.

(21) Appl. No.: 15/637,026

(22) Filed: Jun. 29, 2017

(65) Prior Publication Data
US 2017/0296669 A1 Oct. 19, 2017

Related U.S. Application Data

(62) Division of application No. 13/989,955, filed as application No. PCT/IB2011/055360 on Nov. 29, 2011, now Pat. No. 9,724,421.

(30) Foreign Application Priority Data

Nov. 29, 2010 (CH) ...................... 1997/10

(51) Int. Cl.
| | |
|---|---|
| A61K 47/32 | (2006.01) |
| A61K 9/00 | (2006.01) |
| A61K 9/16 | (2006.01) |
| A61K 31/404 | (2006.01) |
| A61K 31/506 | (2006.01) |

(52) U.S. Cl.
CPC ............ *A61K 47/32* (2013.01); *A61K 9/0019* (2013.01); *A61K 9/1676* (2013.01); *A61K 9/1688* (2013.01); *A61K 31/404* (2013.01); *A61K 31/506* (2013.01)

(58) Field of Classification Search
CPC .................................................. A61K 47/32
See application file for complete search history.

(56) References Cited

FOREIGN PATENT DOCUMENTS

| WO | WO-00/023054 A1 | 4/2000 |
|---|---|---|
| WO | WO-2006/027567 A2 | 3/2006 |
| WO | WO-2007090897 A1 | 8/2007 |

OTHER PUBLICATIONS

Beddy, P., et al. (2009), "Primary embolization of a Symptomatic Gastrointestinal Stromal Tumor" Journal of Vascular and Interventional Radiology, 20(8).
Emoto et al., (2010) "Novel Chemoembolization using calcium-phosphate ceramic microsphere incorporating TNP-470, an Angiogenic agent" Cancer Science, 101:4 984-990.
International Preliminary Report of Patentability dated Jan. 18, 2013 issued in PCT Application No. PCT/IB2011/055360.
International Search Report and Written Opinion dated Mar. 16, 2012 issued in PCT Application No. PCT/IB2011/055360.
Jiang, B., et al. (2005), "Ibuprofen-loaded nanoparticles prepared by a co-precipitation method and their release properties", *International Journal of Pharmaceutics*, 304: 220-230.
Kindler, H., et al. (2009) "6502 a double-blinded, placebo-controlled randomized, phase III study of axitinib (AG-013736; A) plus gemcitabine (G) vs. G plus placebo (P) in advanced pancreatic cancer (PC) patients (pts)" European Journal of Cancer, 7(2): 361-362.
Kruger et al. (2000) "An Angiogenesis Inhibitor in Clinical Development for Cancer" Ecp. Opin. Invest Drugs, 9:6 1383-1396.
Tsochatizis et al., (2010) "Transarterial Chemoembolization, Transarterial Chemotherapy, and Intra-arterial Chemotherapy for Hepatocellular Carcinoma Treatment", Seminars in Oncology, 37: 89-93.
Vandelli, M., et al. (2004), "Microwave-treated gelatin microspheres as drug delivery system", *Journal of Controlled Release*, 96: 67-84.
Poggi, G., et al. "889 chemoembolization with drug-eluting beads: results of a comparison study between hepaspheres™ and DC beads™ loaded with epirubicin", Journal of Hepatology, 52:S346-S347 (2010).

*Primary Examiner* — Jeffrey S Lundgren
*Assistant Examiner* — Tori Strong
(74) *Attorney, Agent, or Firm* — Harness, Dickey & Pierce P.L.C.

(57) ABSTRACT

The invention relates to chemoembolization compositions for anti-angiogenic agent delivery. The invention further relates to a method of preparing chemoembolization compositions and to the use of chemoembolization compositions in the method for treating solid tumour cancers.

33 Claims, 11 Drawing Sheets

CHEMOEMBOLIZATION COMPOSITION COMPRISING ANTI-ANGIOGENIC AGENTS

PRIORITY STATEMENT

This application is a divisonal application of U.S. patent application Ser. No. 13/989,955 which has a filing date of 7 Aug. 2013, which is a national stage application under 35 U.S.C. § 371 of PCT International Application. No. PCT/IB2011/055360 which has an International filing date of 29 Nov. 2011, and which claims the benefit under under 35 U.S.C. § 119 to Switzerland Application No. 01997/10 filed 29 Nov. 2010. The contents of each application recited above are incorporated herein by reference in their entirety.

FIELD OF THE INVENTION

The invention relates to chemoembolization composition for anti-angiogenic agent delivery. The invention further relates to a method of preparing chemoembolization composition and to the use of chemoembolization composition in the method for treating solid tumour cancers.

BACKGROUND OF THE INVENTION

Drug eluting beads (DEBs) have been recently developed as a new mean of delivering chemotherapeutic agents in a targeted and controllable fashion. DEBs, used in chemoembolization therapies, such as transarterial chemo-embolization (TACE), are embolizing beads that can be loaded with chemotherapeutic agents and that can slowly release them in the tumour vasculature with the advantage of lower systemic toxicity and sustained local activity. Thus TACE combines therapeutic effects of peripheral arterial occlusion with the local administration of chemotherapeutic agents. The ideal TACE scheme should allow maximum and sustained concentration of the chemotherapeutic agent within the tumour with minimal systemic exposure combined with calibrated tumour vessel obstruction.

Recently it has been reported that DEBs have the ability to actively sequester doxorubicin hydrochloride from a solution and release it in a controlled and sustained fashion. They have been shown to substantially diminish the amount of chemotherapeutic agent that reaches the systemic circulation, thus significantly increasing the local concentration of the drug and the antitumoral efficacy. For example alginate beads loaded with doxorubicin have been reported (Yao Xue Xue Bao. 2006 August; 41 (8):778-83), or polyvinyl alcohol hydrogel beads modified with sulphonate groups loaded with doxorubicin have been also reported (Clin Cancer Res. 2006 Apr. 15; 12(8):2563-7), for chemoembolization of the liver and demonstrated a sustained delivery in vivo. Comparison of drug loading and delivery of doxorubicin and irinotecan for different beads has been also recently reported (Jordan et al, J Vasc Int Radiol 21:1084-1090, 2010). These systems use the ion-exchange properties of the polymer of beads to sequester cationically charged drugs such as doxorubicin hydrochloride, and provide a method of controlled and sustained post intraarterial delivery to a specific site within the body, in WO 2004/071495 and WO 2006/027567, beads comprising water-insoluble polymer, having an overall anionic charge and electrostatically associated with the polymer an anthracycline or camptothecin compound are disclosed. The DEBs may be used to embolize tumours, for instance a hepatocellular carcinoma. WO 2008/138758 also discloses beads (microspheres) loaded with nemorubicin hydrochloride.

However, preparing drug-loaded beads is not a straightforward procedure, especially if they should be loaded with chemotherapeutic agents of low solubility in aqueous media. This solubility can be insufficient to reach useful therapeutic dose, such as for sorafenib tosylate. In the case where apparent solubility is sufficient to reach useful therapeutic dose, it may appear that some delayed precipitation occurs; making impossible the utilization of such preparation in a clinic setup. For example, sunitinib base or malate can be dissolved in standard media used for loading anthracycline drugs, such as doxorubicine. However in such standard solutions, sunitinib base or malate precipitate within a short period of time which makes loading sunitinib into beads and obtaining stable solutions in drug-loaded beads very problematic. In addition, no liquid oral or parenteral solution of any sunitinib salt is commercially available, that could be used to load DEBs. Only sunitinib suspensions in acidic media have been proposed in the literature for oral route (Navid F et al, Ann Pharmacotherapy 42:962-966, 2008; Sistla A et al Drug Dev Ind Pharm 30(1):19-25, 2004), but this is not suitable for loading DEBs. WO 2007/090897 further discloses a method for loading beads with water insoluble chemotherapeutic agents by using organic solvents. However, such an approach is not adequate for extemporaneous preparation by the medical staff.

Therefore there remains an unmet need to provide drug-loaded beads with chemotherapeutic agents of low aqueous solubility, such as anti-angiogenic agents, more particularly such as sunitinib.

SUMMARY OF THE INVENTION

The Applicants have developed a novel method for loading drug eluting beads with anti-angiogenic agents having low aqueous solubility, such as sunitinib.

Thus the present invention provides a chemoembolization composition for anti-angiogenic agent delivery characterized in that it comprises an anti-angiogenic agent loaded in anionic drug eluting beads, wherein said anti-angiogenic agent is selected from the group comprising sunitinib, angiostatin K1-3, arresten, DL-α-difluoromethyl-ornithine, fumagillin, genistein, staurosporine, (±)-thalidomide, tumstatin, axitinib, bortezomib, bosutinib gefitinib, pazopanib, semaxanib, sorafenib, vandetanib, vatalanib, canertinib, dovitinib, dasatinib, erlotinib, imatinib, lapatinib, masutinib, mubitinib, lestaurtinib, pazopanib, tandutinib, vismodegib, and wherein said anionic drug eluting beads are selected from the group comprising sulphonate-modified polyvinyl alcohol hydrogel beads and carboxyl-modified polyvinyl alcohol-co-sodium acrylate beads.

The present invention further provides a method of preparing chemoembolization composition for anti-angiogenic agent delivery characterized in that said method comprises the following steps:

a) providing drug eluting beads, selected from the group comprising sulphonate-modified polyvinyl alcohol hydrogel beads or carboxyl-modified polyvinyl alcohol-co-sodium acrylate beads, b) preparing an aqueous solution of anti-angiogenic agent, wherein said aqueous solution has a pH of 2.5 to 5 and wherein said anti-angiogenic agent has low aqueous solubility of less than 5 mg/mL and being positively charged, c) adding a sugar or polyol solution to the anti-angiogenic solution of step b)

d) contacting anti-angiogenic solution of step c) with drug eluting beads of step a).

The present invention also provides the chemoembolization composition of the invention for use in the method for treating solid tumour cancers.

DETAILED DESCRIPTION OF THE INVENTION

Figure 1:
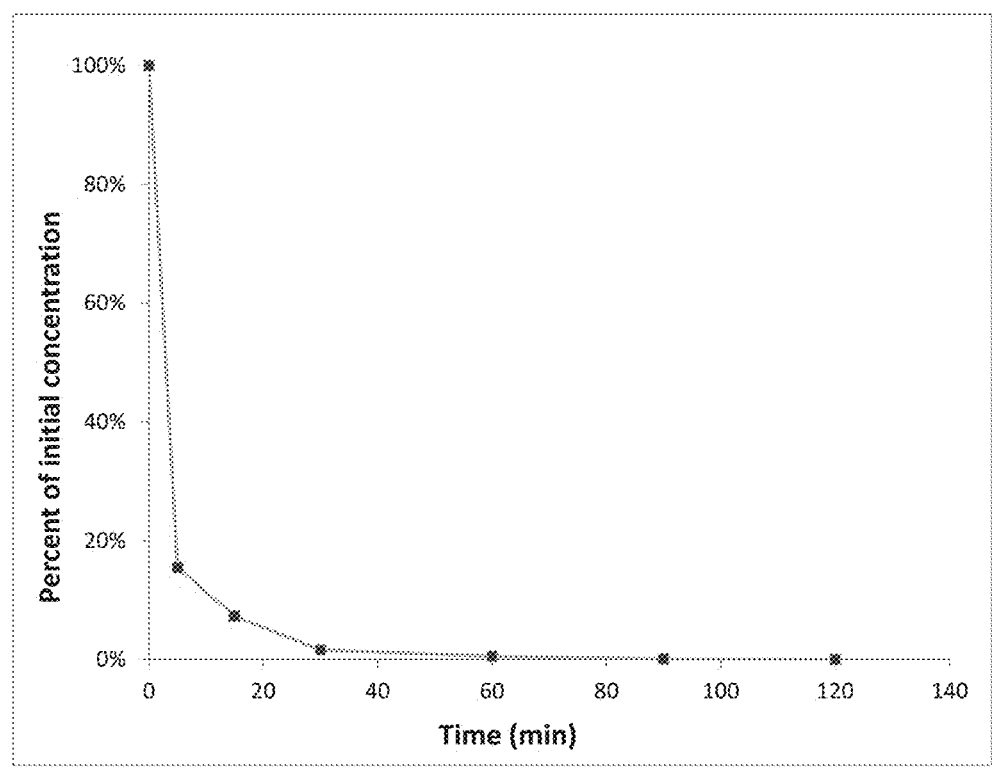
FIG. 1 shows the percentage of remaining drug in 2 mL of supernatant solution having an initial concentration of 10 mg/mL sunitinib. Complete absorption of 20 mg sunitinib per g of bead is observed already after 90 min.

Although methods and materials similar or equivalent to those described herein can be used in the practice or testing of the present invention, suitable methods and materials are described below. All publications, patent applications, patents, and other references mentioned herein are incorporated by reference in their entirety. The publications and applications discussed herein are provided solely for their disclosure prior to the filing date of the present application. Nothing herein is to be construed as an admission that the present invention is not entitled to antedate such publication by virtue of prior invention. In addition, the materials, methods, and examples are illustrative only and are not intended to be limiting.

In the case of conflict, the present specification, including definitions, will control. Unless defined otherwise, all technical and scientific terms used herein have the same meaning as is commonly understood by one of skill in art to which the subject matter herein belongs. As used herein, the following definitions are supplied in order to facilitate the understanding of the present invention.

The term "comprise" is generally used in the sense of include, that is to say permitting the presence of one or more features or components.

As used in the specification and claims, the singular form "a", "an" and "the" include plural references unless the context clearly dictates otherwise.

As used herein the terms "subject" or "patient" are well-recognized in the art, and, are used herein to refer to a mammal and most preferably a human. In some embodiments, the subject is a subject in need of treatment or a subject with solid tumour cancers. In other embodiments, the subject can be a subject who has undergone tumour resection or radiotherapy and/or chemotherapy. The term does not denote a particular age or sex. Thus, adult and newborn subjects, whether male or female, are intended to be covered.

It has been demonstrated that ischemia induced by embolization causes an increase in VEGF activity and neoangiogenesis, particularly in the periphery of the tumour. This neoangiogenesis probably accounts for the regrowth of residual tumour cell after treatment by transarterial chemoembolization (LACE). Therefore, the Applicants estimated that TACE could be more efficient when associated with anti VEGF therapy, for example the association of TACE with different anti-angiogenic agents.

The Applicants have developed a chemoembolization therapy which combines therapeutic effects of peripheral arterial occlusion with the local administration of an anti-angiogenic agent. Chemoembolization is a combination of local delivery of chemotherapy and a procedure called embolization to treat solid tumour cancers. Solid tumour cancers that may be treated by chemoembolization are sarcomas, carcinomas and lymphomas. Solid tumours can develop in virtually any tissue or organ, such as lungs, breast, prostate, skin, liver and colon. In a preferred embodiment of the present invention, solid tumour cancers are malignant hypervascularised tumours, such as hepatoma or hepatocellular carcinoma (primary liver cancer) and metastasis (spread) to the liver from: colon cancer, breast cancer, carcinoid tumours and other neuroendocrine tumours, islet cell tumours of the pancreas, ocular melanoma, sarcomas, other vascular primary tumours in the body. Some success has been demonstrated with patients whose cancer has spread to other areas of the body, such as the chest, the kidney, pelvic organs, or oral cavity. Chemoembolization is most beneficial to patients whose disease is predominately malignant hypervascularised tumours, such as liver, whether the tumour began in the liver or spread to the liver (metastasized) from another organ.

In chemoembolization, anti-cancer drugs are injected directly into the blood vessel feeding a cancerous tumour. In addition, synthetic material called an embolic agent, such as beads, is placed inside the blood vessels that supply blood to the tumour, in effect trapping the chemotherapy in the tumour.

As used herein, "injected directly into the blood vessel feeding a cancerous tumour" or "placed inside the blood vessels that supply blood to the tumour" refers to deposition of the embolic agent, such as beads, in an artery sufficiently close to the target tumour. Such deposition can be accomplished by a number of means including, without limitation, the use of catheters and direct injection. Both of these methods of delivering embolic agents, such as beads, to a specific locale in a patient's body are well-known to those skilled in the art.

Depending on the number and type of tumours, chemoembolization may be used as the sole treatment or may be combined with other treatment options such as surgery (tumour resection), standard chemotherapy and/or radiotherapy. For example chemoembolization can be applied before and/or after surgery (tumour resection), standard chemotherapy and/or radiotherapy.

The term "standard chemotherapy" generally refers to a treatment of a cancer using specific chemotherapeutic/chemical agents. A chemotherapeutic agent refers to a pharmaceutical agent generally used for treating cancer. The chemotherapeutic agents for treating cancer interfering with DNA synthesis include, for example, cisplatin, carboplatin, etoposide, vincristine, cyclophosphamide, doxorubicin, ifosfamide, paclitaxel, gemcitabine, docetaxel, and irinotecan and platinum-based anti-cancer agents, including cisplatin and carboplatin. Other anti cancer drugs comprise tyrosine kinase inhibitors such as gefitinib, imatinib; famesyl transferase inhibitors including lonafarnib; inhibitors of mammalian targets of rapamycin (mTOR) such as evereolimus; inhibitors of PKC; PI3K and AKT and monoclonal antibodies targeted against cellular receptors to signaling molecules such as bevacizumab, cetuximab, panitumumaband trastazumab.

The term "standard radiotherapy" refers to the use of ionizing radiation as part of cancer treatment to control malignant cells. Preferably the ionizing radiation is x rays or γ-rays. It is also common to combine radiotherapy with surgery, chemotherapy, hormone therapy, or combinations thereof. Most common cancer types can be usually treated with radiotherapy. The precise treatment intent (curative, adjuvant, neoadjuvant or palliative) will depend on the tumour type, location, and stage, as well as the general health of the subject in need thereof.

The standard chemotherapy and radiotherapy can be also the concomitant chemo-radiotherapy. The term "concomitant chemo-radiotherapy" is used when these two treatments (chemotherapy and radiotherapy) are given either at the same time, or almost at the same time, for instance one after the other, or on the same day.

The present invention provides a chemoembolization composition for anti-angiogenic agent delivery characterized in that it comprises an anti-angiogenic agent loaded in anionic drug eluting beads,
   wherein said anti-angiogenic agent is selected from the group comprising sunitinib, angiostatin K1-3, arresten, DL-α-difluoromethyl-ornithine, fumagillin, genistein, staurosporine, (±)-thalidomide, tumstatin, axitinib, bortezomib, bosutinib gefitinib, pazopanib, semaxanib, sorafenib, vandetanib, vatalanib, canertinib, dovitinib, dasatinib, erlotinib, imatinib, lapatinib, masutinib, mubitinib, lestaurtinib, pazopanib, tandutinib, vismodegib, and
   wherein said anionic drug eluting beads are selected from the group comprising sulphonate-modified polyvinyl alcohol hydrogel beads and carboxyl-modified polyvinyl alcohol-co-sodium acrylate beads.

Preferably, said anti-angiogenic agent is sunitinib or imatinib. Also preferably said anionic drug eluting beads are sulphonate-modified polyvinyl alcohol hydrogel beads or carboxyl-modified polyvinyl alcohol-co-sodium acrylate beads. Most preferably said anionic drug eluting beads are sulphonate-modified polyvinyl alcohol hydrogel beads In a further embodiment, the present invention also relates to a chemoembolization composition for anti-angiogenic agent delivery characterized in that it comprises an anti-angiogenic agent, having low aqueous solubility of less than 5 mg/mL and being positively charged, loaded in anionic drug eluting beads, wherein said anionic drug eluting beads are selected from the group comprising sulphonate-modified polyvinyl alcohol hydrogel beads and carboxyl-modified polyvinyl alcohol-co-sodium acrylate beads.

The term "low aqueous solubility" refers to an anti-angiogenic agent of the invention, either salt or acidified free base thereof, having solubility in the sugar-free medium less than the therapeutical dose that can be incorporated in the drug eluting beads (microspheres) when said drug eluting beads are contacted with the anti-angiogenic agent solution. Typically, low aqueous solubility in the present application refers to a compound having a solubility in water (sugar-free) which is less than or equal to 5 mg/mL, when measured at ambient temperature (i.e. 18-27° C.).

The terms "anti-angiogenic agent" and "angiogenesis inhibitor", either salt of free base thereof, are used interchangeably herein and include any agent that is capable of preventing or inhibiting the formation of blood vessels, in the context of the present invention, specific examples of anti-angiogenic agents include, but are not limited to, sunitinib, angiostatin K1-3, arresten, anti-angiogenic antithrombin (aaAT), canstatin, DL-α-difluoromethyl-ornithine, endostatin, fumagillin, genistein, minocycline, staurosporine, (±)-thalidomide, tumstatin, axitinib, bortezomib, bosutinib gefitinib, pazopanib, semaxanib, sorafenib, vandetanib, vatalanib, canertinib, dovitinib, dasatinib, erlotinib, imatinib, lapatinib, masutinib, mubitinib, nilotinib, lestaurtinib, pazopanib, tandutinib, vismodegib.

Preferably anti-angiogenic agents are selected from the group comprising sunitinib, angiostatin K1-3, arresten, DL-α-difluoromethyl-ornithine, fumagillin, genistein, staurosporine, (±)-thalidomide, tumstatin, axitinib, bortezomib, bosutinib gefitinib, pazopanib, semaxanib, sorafenib, vandetanib, vatalanib, canertinib, dovitinib, dasatinib, erlotinib, imatinib, lapatinib, masutinib, mubitinib, lestaurtinib, pazopanib, tandutinib, vismodegib.

More preferably the anti-angiogenic agent is sunitinib and imatinib.

The present invention has been found to be of utility for formulating chemoembolization compositions containing chemotherapeutic agents having anti-angiogenic properties and low aqueous solubility. The invention is of particular utility for, for example, sunitinib.

Sunitinib is a small-molecule that inhibits multiple receptor tyrosine kinases (RTK) such as platelet-derived growth factor receptor (PDGF-Rs) and vascular endothelial growth factor receptors (VEGFRs), which play a role in both tumour angiogenesis and tumour cell proliferation. sunitinib also inhibits other RTK such as KIT (CD117) that, when improperly activated by mutations, drives the majority of gastrointestinal stromal cell tumours. In these tumours, sunitinib has been recommended as a second-line therapy for patients whose tumours are resistant to imatinib, or in patients who become intolerant to the drug. In addition, sunitinib also inhibits other RTKs like RET, CSF-1R, FLT3. The simultaneous inhibition of these targets therefore leads to a reduction of tumour vascularization and to an increase cancer cell death, and ultimately tumour shrinkage.

Sunitinib was approved by the FDA for the treatment of renal cell carcinoma (RCC) and imatinib-resistant gastrointestinal stromal tumour (GIST) on Jan. 26, 2006. Sunitinib demonstrated anti-tumour activity in preclinical studies in models of colorectal cancer (CRC), non small cell lung cancer (NSCLC), melanoma, renal cell carcinoma (RCC) and squamous cell carcinoma (SCC). Clinical activity was demonstrated in neuroendocrine, colon and breast cancer in phase II studies. The currently approved starting oral dose of sunitinib is 50 mg/day, which is sufficient to produce plasma concentrations of at least 50 ng/ml (the minimum concentration predicted from chemical- and cellular-based assays to inhibit VEGFR and PDGFR).

The fact that sunitinib targets many different receptors, results in many side effects. Hypertension and asthenia appear to be the most common adverse effects with sunitinib. Diarrhoea, anorexia, disgeusia, stomatitis and hand and foot syndrom (HFS) are the other clinically relevant side effects. HFS may require treatment discontinuation for a few days and/or dose reduction. Fatigue may be related to the development of hypothyroidism during sunitinib therapy. Dose reductions are required in 50% of patients treated for RCC in order to manage the significant toxicities of this agent. Serious (grade 3 or 4) adverse events occur in ≤10% of patients. Laboratory abnormalities associated with sunitinib therapy include increased lipase and amylase levels, reduced neutrophils, lymphocytes, and platelets counts. Therefore, the administration of sunitinib via DEBs could reduce the systemic toxicity while maintaining local anti tumour efficacy, provided that sunitinib does not precipitate in drug eluting beads.

Drug eluting beads (DEBs) are spherical or substantially spherical beads (microspheres), based on a hydrophilic, albeit water-insoluble, biocompatible polymeric material, such as modified polyvinyl alcohol (PVA) or acrylic copolymer. These polymers bear negatively charged groups for retaining positively charged chemotherapeutic agents, such as anti-angiogenic agents. Typically, the beads (microspheres) have sizes when equilibrated in water at 37° C., in the range 1-1000 μm, more preferably in the range 50 to 500 μm, most preferably in the range 100-300 μm. The diameter is preferably determined by measurement of the beads size prior to loading with the positively charged chemotherapeutic agent.

Specific examples of drug eluting beads according to the present invention include, but are not limited to, sulphonate-modified polyvinyl alcohol hydrogel beads and carboxyl-modified polyvinyl alcohol-co-sodium acrylate beads.

Sulphonate-modified polyvinyl alcohol hydrogel, used to prepare beads known as DC Bear (Biocompatibles), is a microspherical soft deformable embolisation material FDA approved for the treatment of hypervascular tumours and arterio-venous malformations. It is composed of a polyvinyl alcohol (PVA) polymer hydrogel that has been modified by the addition of a sulphonic acid-containing component (2-acrylamido-2-methylpropane sulphonic acid), known as PVA (with N-acryloyl-aminoacetaldehyde dimethyl acetal) copolymerized with 2-acrylamido-2 methylpropanesulfonate sodium salt, and formulated by inverse suspension polymerisation into beads of varying size from 50 to 1200 μm. The presence of the negative charged moiety enables the beads to interact with oppositely-charged chemotherapeutic agents. The sulphonate-modified polyvinyl alcohol hydrogel beads are usually stored in a phosphate packing solution.

Carboxyl-modified polyvinyl alcohol-co-sodium acrylate beads, known as Hepasphere™ in Europe or Quadrasphere™ in the US (Biosphere Medical) are precisely calibrated, spherical, hydrophilic, macroporous beads. They are supplied as a dry product that can be rehydrated before use. The elastic properties allow the temporary deformation of the sphere, which facilitates the passage through small delivery systems. They allow a complete occlusion of hypervascularized tumours or arteriovenous malformations. The polymer is modified with carboxyl groups, facilitating cationic drug loading.

According to the present invention, BeadBlock™ beads (Biocompatibles) can be also used. These beads are also sulphonate-modified polyvinyl alcohol hydrogel beads, but contain less sulphonate groups than the above-mentioned DC Bead™.

According to the present invention, the positively (cationically) charged anti-angiogenic agent is associated with the anionic beads preferably so as to allow controlled release of the anti-angiogenic agent over a period. This period may be from several minutes to weeks, preferably at least up to a few days, preferably up to 72 hours. The anti-angiogenic agent is electrostatically bonded to the polymer of beads. The presence of anionic groups in the beads allows control of release of positively (cationically) charged anti-angiogenic agent. It is important that the anti-angiogenic agent is not covalently attached to the polymer matrix.

The present invention further provides a method of preparing chemoembolization composition for anti-angiogenic agent delivery characterized in that said method comprises the following steps:

a) providing drug eluting beads, selected from the group comprising sulphonate-modified polyvinyl alcohol hydrogel beads or carboxyl-modified polyvinyl alcohol-co-sodium acrylate beads, b) preparing an aqueous solution of anti-angiogenic agent, wherein said aqueous solution has a pH of 2.5 to 5 and wherein said anti-angiogenic agent has low aqueous solubility of less than 5 mg/mL and being positively charged, c) adding a sugar or polyol solution to the anti-angiogenic solution of step b)

d) contacting anti-angiogenic solution of step c) with drug eluting beads of step a).

Optionally saline solution is removed from anionic drug eluting beads in step a).

Usually step d) is carried out by suspending drug eluting beads in anti-angiogenic solution of step c). Typically drug eluting beads are left in contact with anti-angiogenic solution during 1 to 5 hours, preferably 1 hour 30 minutes and 3 hours 30 minutes, more preferably during 2 hours.

Preferably, said anti-angiogenic agent is selected from the group comprising sunitinib, angiostatin K1-3, arresten, anti-angiogenic antithrombin (aaAT), canstatin, DL-α-difluoromethyl-ornithine, endostatin, fumagillin, genistein, minocycline, staurosporine, (±)-thalidomide, tumstatin, axitinib, bortezomib, bosutinib gefitinib, pazopanib, semaxanib, sorafenib, vandetanib, vatalanib, canertinib, dovitinib, dasatinib, erlotinib, imatinib, lapatinib, masutinib, mubitinib, nilotinib, lestaurtinib, pazopanib, tandutinib, vismodegib.

More preferably said anti-angiogenic agents are selected from the group comprising sunitinib, angiostatin K1-3, arresten, DL-α-difluoromethyl-ornithine, fumagillin, genistein, staurosporine, (±)-thalidomide, tumstatin, axitinib, bortezomib, bosutinib gefitinib; pazopanib, semaxanib, sorafenib, vandetanib, vatalanib, canertinib, dovitinib, dasatinib, erlotinib, imatinib, lapatinib, masutinib, mubitinib, lestaurtinib, pazopanib, tandutinib, vismodegib.

Most preferably said anti-angiogenic agent is sunitinib or imatinib.

The Applicants have developed an advantageous method for loading anti-angiogenic agents, having low aqueous solubility of less than 5 mg/mL, into drug eluting beads. According to this method, anti-angiogenic agent may be incorporated into the drug eluting beads by contacting swollen beads suspended in a continuous liquid vehicle, such as water, with an aqueous sugar or polyol solution of the anti-angiogenic agent, over a period of time, typically 2 hours, whereby drug becomes absorbed into the body of the beads.

According to the present invention, the aqueous sugar solution of the anti-angiogenic agent is typically prepared by dissolving the anti-angiogenic agent in water, if necessary by acidification with any suitable acid, in order to obtain an aqueous solution having a pH of 2.5 to 5, preferably pH 3 to 4.5, Typically the concentration of the anti-angiogenic agent is in the range of 0 to 25 mg/mL, preferably 1 to 25 mg/mL or 1 to 15 mg/mL, more preferably 2 to 25 mg/mL or 2 to 15 mg/mL, most preferably 5 to 15 mg/mL. High concentration such as 15 to 25 mg/mL of anti-angiogenic agent are also encompassed by the present invention. The solution is gently shaken until the complete dissolution of the anti-angiogenic agent. Then a sugar or a polyol is added to achieve a solution with suitable osmotic pressure.

A suitable acid can be any mineral acid, for example hydrochloric acid, sulphuric acid or nitric acid, or any organic acid, for example lactic acid, acetic acid or formic acid. Preferably the acid is hydrochloric acid. For example for sunitinib, typically HCl 0.1N solution is used, in an equimolar quantity or slightly higher quantity to sunitinib, such as 1-1.05 mole of HCl per 1 mole of sunitinib.

According to the present invention, a sugar or polyol is selected from the group comprising glucose, sucrose, dextran, mannitol, sorbitol or trehalose. Typically sugar or polyol solution is at 2-15%, preferably 3 to 7% and more preferably at 5%. Preferably sugar solution is 5% glucose solution.

The Applicants have found that surprisingly, in presence of the sugar, preferably at 5% glucose, sunitinib solution was shown to be stable, without any precipitation, in contrast to saline or hydrochloric acid solutions. Advantageously, this solution is isotonic to human plasma and it is safe for the parenteral applications. Noteworthy, the sugar is not limited to glucose. Other sugars or polyol could be used such as sucrose, dextran, mannitol, sorbitol or trehalose.

The swelling vehicle may subsequently be removed or, conveniently, may be retained with the beads as part of the product.

The swollen beads may be used in swollen form in the form of slurry, i.e. without any or much liquid outside the swollen beads. Indeed, in order to increase the efficiency of loading, it was found preferable to remove the saline solution, typically sodium phosphate solution, from the bead solution to leave slurry, before contacting swollen beads with the aqueous sugar solution of the anti-angiogenic agent. Thus optionally, the saline solution is removed from anionic drug eluting beads in step a).

Alternatively, the drug-loaded beads can be removed from any remaining drug loading solution and the beads dried by any of the classical techniques employed to dry pharmaceutical-based products. This could include, but is not limited to, air drying at room or elevated temperatures or under reduced pressure or vacuum; classical freeze-drying; atmospheric pressure-freeze drying; solution enhanced dispersion of supercritical fluids (SEDS). Alternatively the drug-loaded beads may be dehydrated using an organic solvent to replace water in a series of steps, followed by evaporation of the more volatile organic solvent. A solvent should be selected which is a non-solvent for the drug.

A typical classical freeze-drying process might proceed as follows: the sample is aliquoted into partially stoppered glass vials, which are placed on a cooled, temperature controlled shelf within the freeze dryer. The shelf temperature is reduced and the sample is frozen to a uniform, defined temperature. After complete freezing, the pressure in the dryer is lowered to a defined pressure to initiate primary drying. During the primary drying, water vapour is progressively removed from the frozen mass by sublimation whilst the shelf temperature is controlled at a constant, low temperature. Secondary drying is initiated by increasing the shelf temperature and reducing the chamber pressure further so that water absorbed to the semi-dried mass can be removed until the residual water content decreases to the desired level. The vials can be sealed, in situ, under a protective atmosphere if required.

Atmospheric pressure freeze-drying is accomplished by rapidly circulating very dry air over a frozen product. In comparison with the classical freeze-drying process, freeze-drying without a vacuum has a number of advantages. The circulating dry gas provides improved heat and mass transfer from the frozen sample. Of particular interest is the fact that by using atmospheric spray-drying processes, instead of a cake, a fine, free-flowing powder is obtained. Particles can be obtained which have submicron diameters; this is ten-fold smaller than can be generally obtained by milling. The particulate nature, with its high surface area results in an easily rehydratable product.

Although the chemoembolization composition of the invention may be made up from beads and canonically charged chemotherapeutic agent immediately before administration, it is also possible that the chemoembolization composition is supplied pre-loaded with the drug. For the latter case, dried drug-loaded beads may be hydrated immediately before use. Alternatively the chemoembolization composition which is supplied may be fully compounded and preferably comprises drug eluting beads with absorbed or adsorbed anti angiogenic agent and imbibed aqueous sugar solution.

The level of anti-angiogenic agent in the chemoembolization composition of the invention, which is administered, is preferably in the range 0.1 to 500 mg per ml composition, preferably 10 to 100 mg per ml. Preferably the treatment is repeated one to five times and for each dose the amount of anti-angiogenic agent administered is in the range 0.1 to 100 mg per ml, preferably 10 to 100 mg per ml. The amount of the chemoembolization composition administered in a normal treatment is in the range 1 to 6 ml. The total amount of anti-angiogenic agent administered per dose is preferably in the range 10 to 1000 mg, more preferably 25 to 250 mg. Based on the release data as shown in the Examples below, the Applicants believe this will give therapeutically effective concentrations in the tumour and that significant levels of intracellular delivery should take place whereby a therapeutic effect will be achieved. The adverse systemic side effects of anti-angiogenic agent administration should be avoided.

The present invention further provides the chemoembolization composition of the invention for use in the method for treating solid tumour cancers.

In a preferred embodiment of the present invention, solid tumour cancers are malignant hypervascularised tumours, such as hepatoma or hepatocellular carcinoma (primary liver cancer) and metastasis (spread) to the liver from: colon cancer, breast cancer, GIST liver metastasis, renal cancer, carcinoid tumours and other neuroendocrine tumours, islet cell tumours of the pancreas, ocular melanoma, sarcomas, other vascular primary tumours in the body.

Thus preferably said malignant hypervascularised tumours are selected from the group comprising hepatocellular carcinoma (HCC), liver metastasis, cholangiomas, neuroendorine tumours, GIST liver metastasis and renal cancer.

The present invention also provides a method of treatment of solid tumour cancers in a subject suffering therefrom comprising administering a therapeutically effective amount of the chemoembolization composition of the invention. Preferably said solid tumour cancers are malignant hypervascularised tumours. More preferably said malignant hypervascularised tumours are selected from the group comprising hepatocellular carcinoma (HCC), liver metastasis, cholangiomas, neuroendorine tumours, GIST liver metastasis and renal cancer.

The method of this invention can be used to treat any solid tumour cancer to which blood is supplied by a dedicated, relatively reachable artery such as the renal, hepatic, pulmonary and cardiac arteries. In an aspect of this invention, the solid tumour cancer is a hepatocellular carcinoma.

"Treatment" refers to both therapeutic treatment and prophylactic or preventative measures. Those in need of treatment include those already with the disorder, for example solid tumour cancer, as well as those in which the disorder, for example solid tumour cancer, is to be prevented. Hence, the mammal, preferably human, to be treated herein may have been diagnosed as having the disorder, for example solid tumour cancer, or may be predisposed or susceptible to the disorder, for example solid tumour cancer, "Mammal" for purposes of treatment refers to any animal classified as a mammal, including humans, domestic and farm animals or pet animals, such as dogs, horses, cats, cows, monkeys etc. Preferably, the mammal is human.

The term "therapeutically effective amount" refers to an amount of a chemoembolization composition effective to treat a disease or disorder in a mammal. In the case of solid tumour cancer, the therapeutically effective amount of the chemoembolization composition may reduce the tumour size; inhibit (i.e., slow to some extent and preferably stop) cancer cell infiltration into peripheral organs; inhibit (i.e., slow to some extent and preferably stop) tumour metastasis; inhibit, to some extent, tumour growth; and/or relieve to some extent one or more of the symptoms associated with the solid tumour cancer. To the extent the chemoembolization composition of the present invention may prevent growth and/or kill existing cancer cells, it may be cytostatic and/or cytatoxic. The phrase "therapeutically effective amount" is used herein to mean an amount sufficient to prevent, or preferably reduce by at least about 30 percent, preferably by at least 50 percent, preferably by at least 70 percent, preferably by at least 80 percent, preferably by at least 90%, a clinically significant change in the growth or progression or mitotic activity of a target cellular mass, group of cancer cells or other feature of pathology.

The daily dose of the chemoembolization composition of the present invention will necessarily be varied depending upon the host treated, the particular route of administration, and the severity and kind of the illness being treated. Accordingly the optimum dosage may be determined by the practitioner Who is treating any particular patient. Further, it is noted that the clinician or treating physician will know how and when to start, interrupt, adjust, or terminate therapy in conjunction with individual patient response. For any chemoembolization composition used in the method of the present invention, a therapeutically effective dose can be estimated initially from cell culture assays, animal models, or microdosing of human subjects.

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended Claims, and all changes which come within the meaning and range of equivalency are intended to be embraced therein.

The foregoing description will be more fully understood with reference to the following Examples. Such Examples are, however, exemplary of methods of practising the present invention and are not intended to limit the scope of the invention.

EXAMPLES

Example 1: Sunitinib Loading in the DEBs

A vial of DCbead™ (100-300 microns diameter, Biocompatibles UK) was used, after removing as much saline supernatant as possible (ca. 6 mL) from the vial. Approximately 2 mL of beads was left at the bottom of the vial. 4 ml of a 10 mg/ml solution of sunitinib base was prepared as follows: to 40 mg of sunitinib base (i.e. $1.3 \cdot 10^{-4}$ mol) was added 1.4 mL of HCl 0.1 N (i.e. an 1.05 mole ratio to sunitinib). The sunitinib was gently shaken until complete dissolution. Then, a 5% w/w glucose solution was added to reach a final volume of 4 mL corresponding to a sunitinib concentration of 10 mg/mL.

The solution was added to the DCbead™ vial, gently shaken once, and left at room temperature for two hours. Aliquots were drawn at different time points for spectrophotometric titration at 430 nm. The percentage of remaining supernatant concentration is shown of FIG. 1. Almost all (>98%) the drug disappeared from the supernatant, indicating progressive loading into the beads. Finally, a drug amount of 20 mg sunitinib per g of DCbead™ was attained. This is designed hereafter as bead loading (in mg of sunitinib per g of beads).

Example 2: Variations of Drug Loading Protocol

Figure 2:
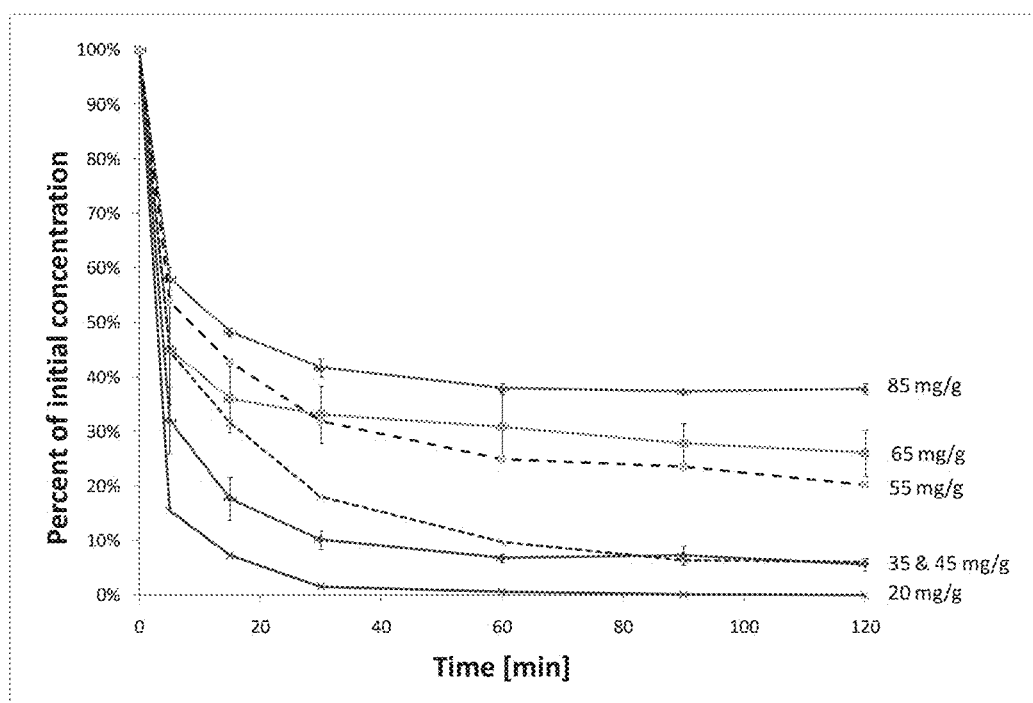
FIG. 2 shows the percentage of remaining drug in different volumes of 10 mg/ml sunitinib solution used for incubation of 1 g DCbead. The legend on the right indicates the initial amount of drug initially present in the incubation medium in mg, per g of DCbead.

The loading protocol of example 1 was repeated, adding various volume of sunitinib solution at 10 mg/mL to the DCbead™ vial, therefore resulting in different nominal bead loadings, from 20 mg per g of DCbead™ to 85 mg per g of DCbead™. The time evolution of the supernatant concentration is illustrated in FIG. 2. The percentage of drug incorporated in the bead after 2 hours incubation, relative to the drug contained in the solution, decreased with increasing volume of sunitinib solution. These results show that high drug payloads could be achieved in 2-hr loading period.

Example 3: Drug Release Properties

Figure 3:
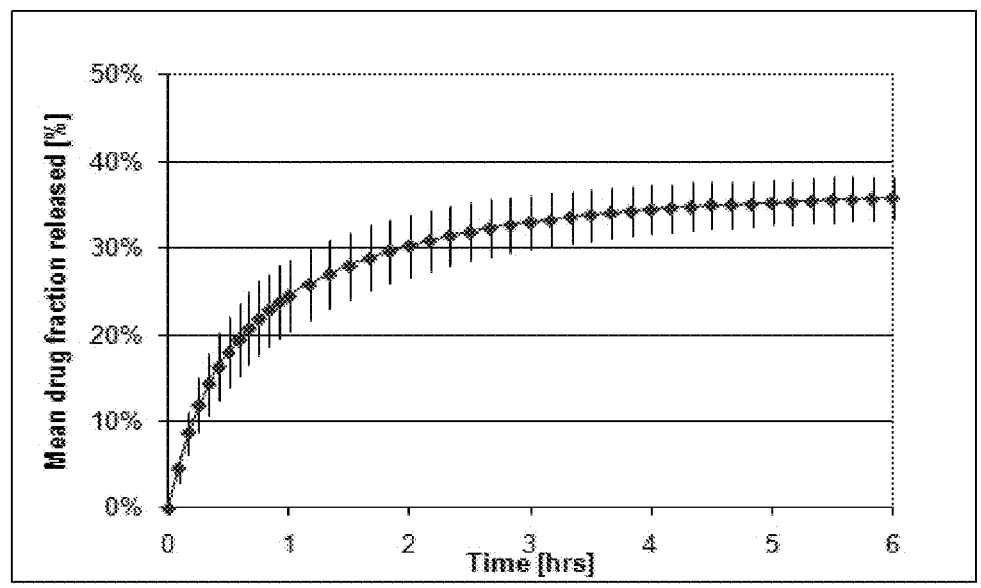
FIG. 3 shows sunitinib released by loaded. DCbead in 30 mL of NaCl 0.9%, using the USP 4 flow-through method. Partial release is attributed to the NaCl-drug ionic exchange mechanism. The 1.3 hr-period necessary to reach 75% of the plateau concentration indicates a gradual release of the drug.
Figure 4:
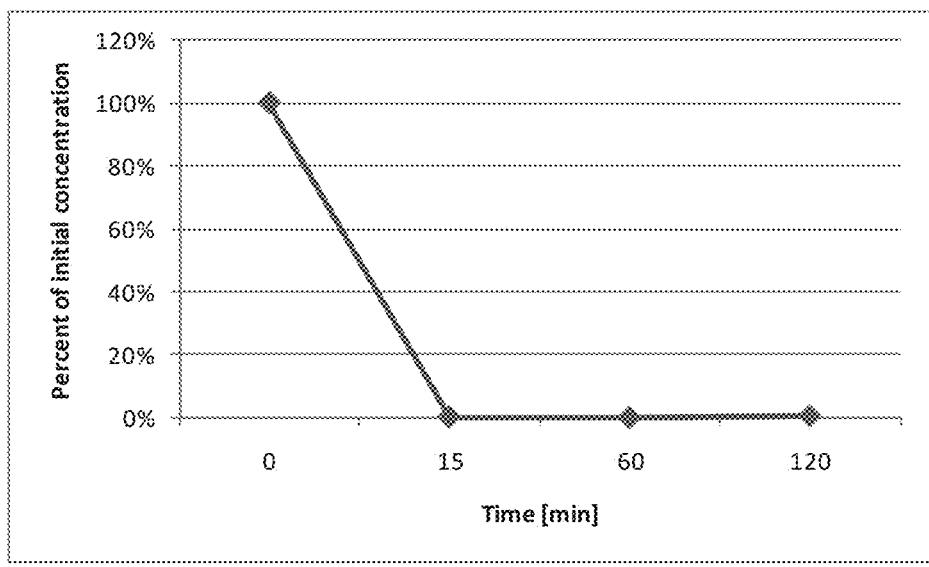
FIG. 4 shows percentage of remaining supernatant concentration for Quadrasphere loading of 25 mg sunitinib per mg of dry microsphere.
Figure 5:
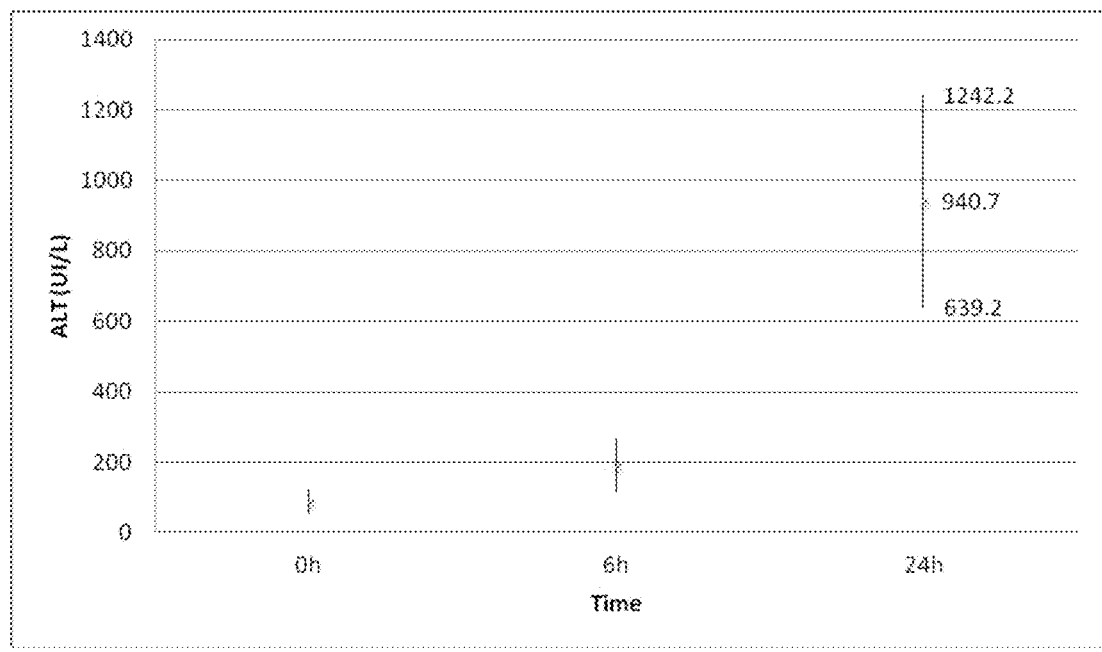
FIG. 5 shows mean ALT level (UI/L) 6 and 24 hours after intra arterial administration of 2 ml DC Beads loaded with 6 mg of sunitinib in the common hepatic artery in a rabbit model.
Figure 6:
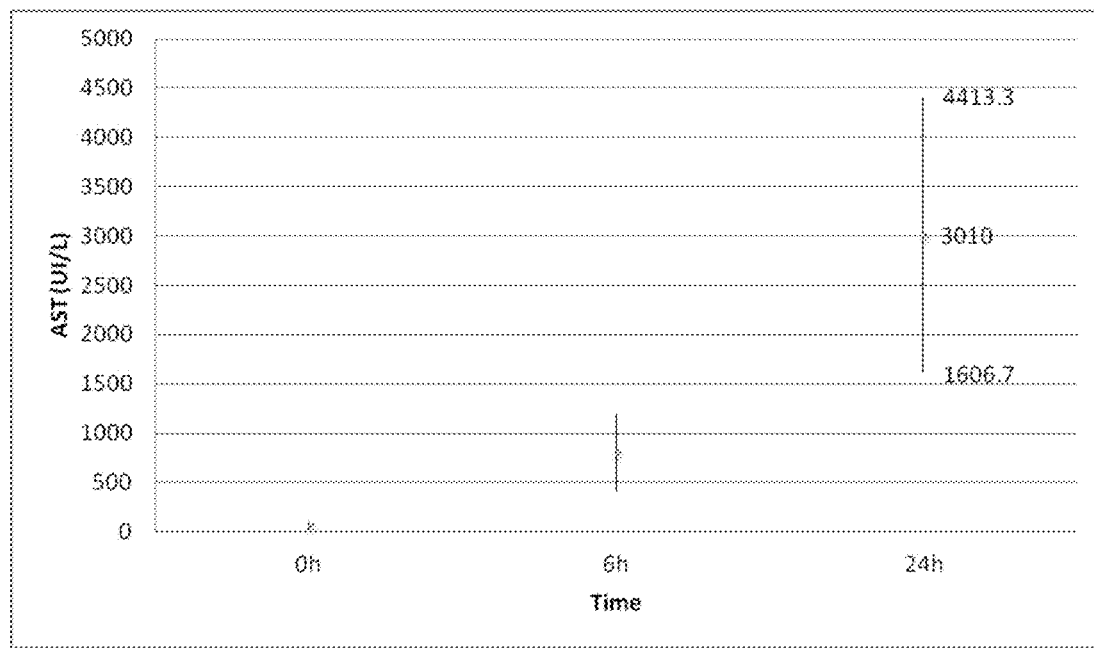
FIG. 6 shows mean AST level (UI/L) 6 and 24 hours after intra arterial administration of 2 ml DC Beads loaded with 6 mg of sunitinib in the common hepatic artery in a rabbit model.
Figure 7:
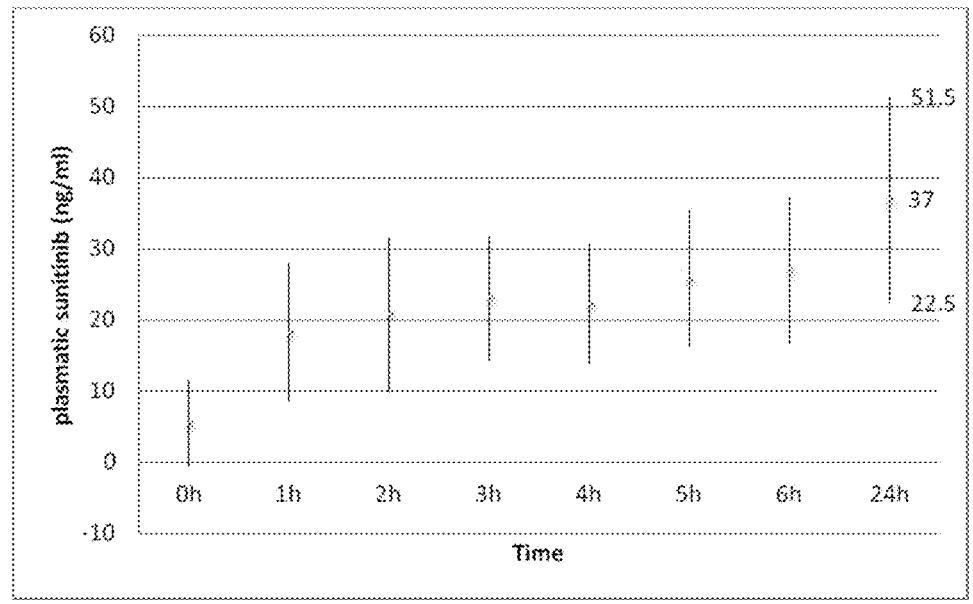
FIG. 7 Plasmatic sunitinib levels (ng/ml) after intra arterial administration of 2 ml DC Beads loaded with 6 mg of sunitinib in the common hepatic artery in 9 rabbits.
Figure 8:
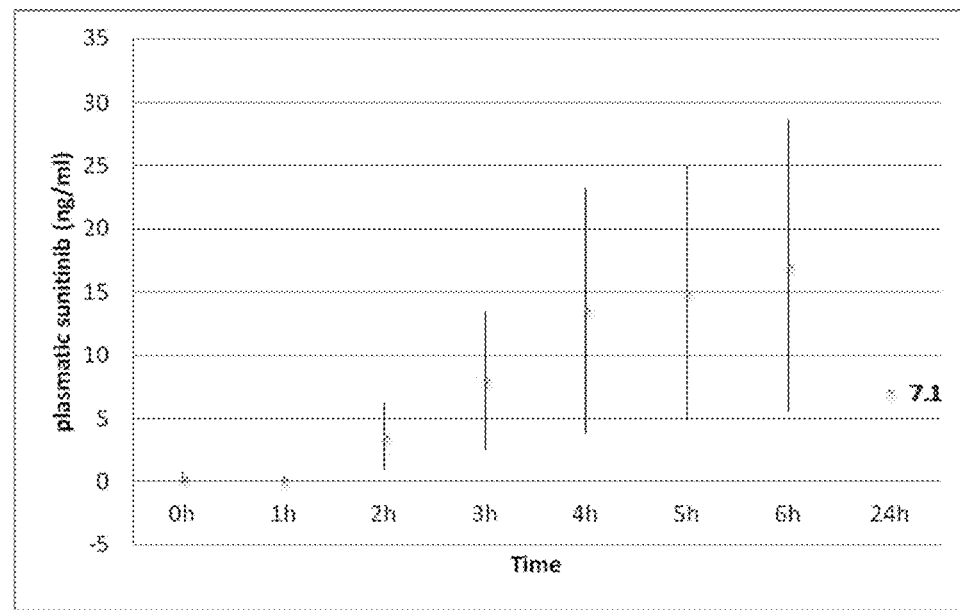
FIG. 8 Plasmatic sunitinib levels (ng/ml) after oral administration of 6 mg of in 3 rabbits.
Figure 9:
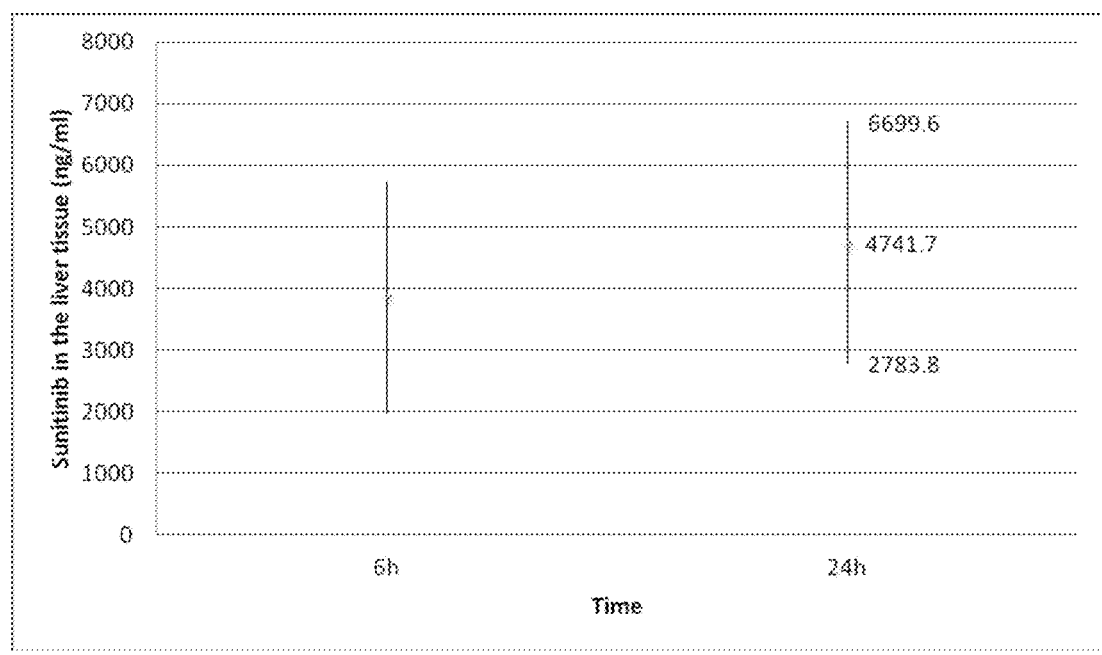
FIG. 9 shows measurements of sunitinib levels (ng/ml) in the liver 6 hours (n=1) and 24 hours (n=3) after administration of 2 ml DC Beads loaded with 6 mg of sunitinib in the common hepatic artery.
Figure 10:
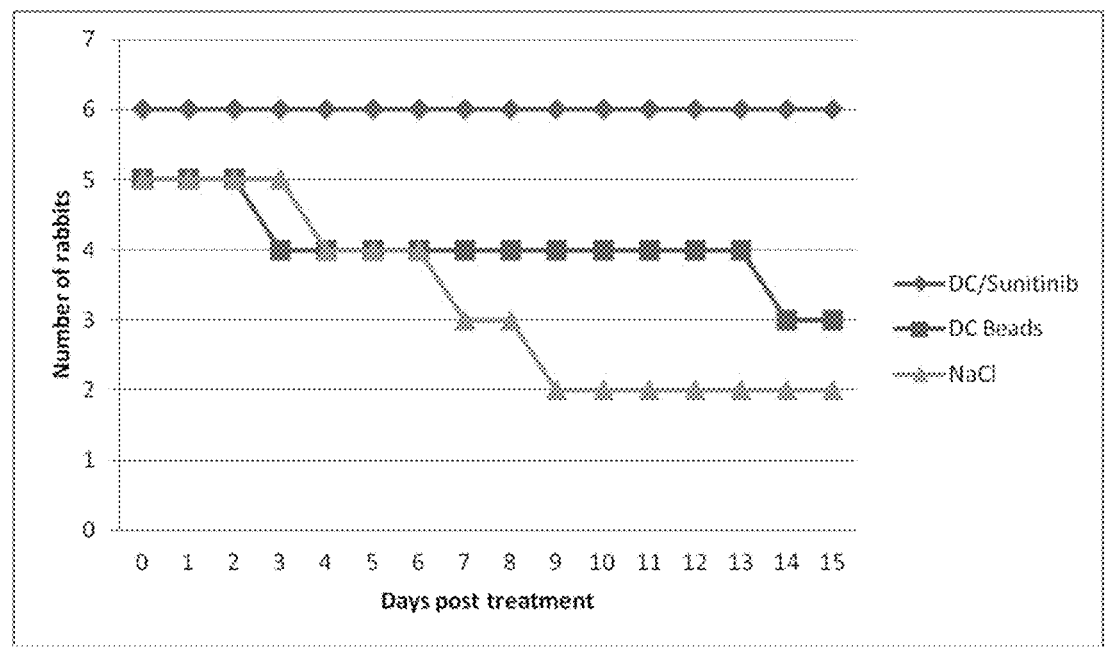
FIG. 10 shows the survival curves of rabbits in the 3 groups treated respectively with DC Beads loaded with sunitinib 1.5 mg (group 1, n=6), DC Beads alone (group 2, n=5), and NaCl injected directly in the arterial branch supplying the left liver lobe.
Figure 11:
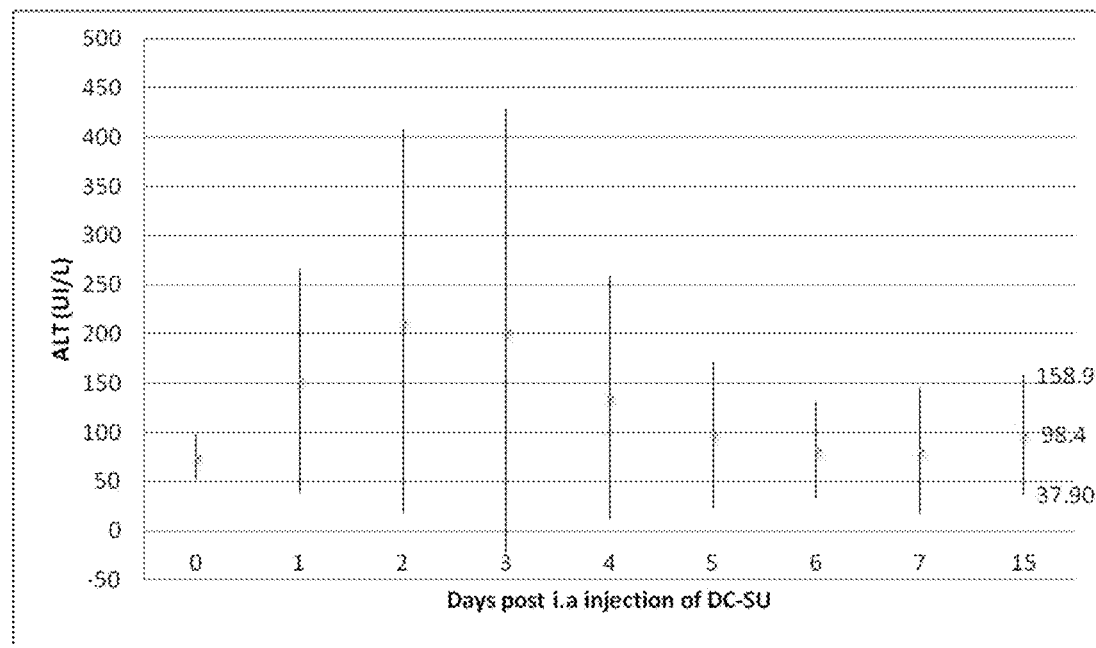
FIG. 11 shows mean ALT level (UI/L) after intra arterial administration of 0.05 ml DC Beads loaded with 1.5 mg of sunitinib in the arterial branch supplying the left lateral lobe of the liver in a rabbit model (group 1).
Figure 12:
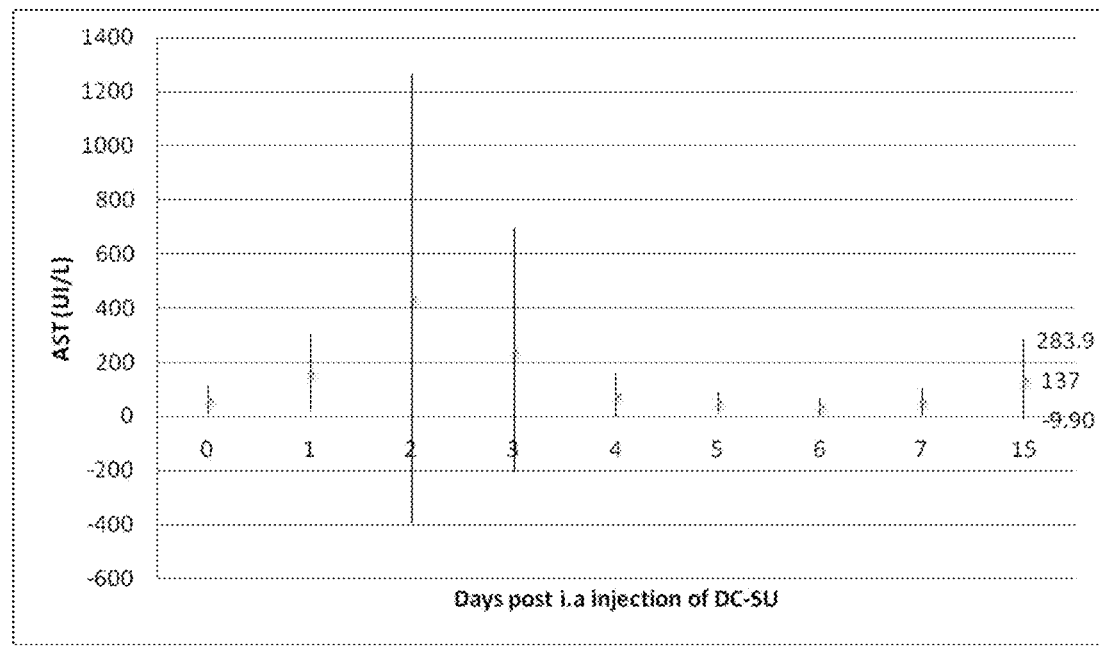
FIG. 12 shows mean AST level (UI/L) after intra arterial administration of 0.05 ml DC Beads loaded with 1.5 mg of sunitinib in the arterial branch supplying the left lateral lobe of the liver in a rabbit model (group 1).
Figure 13:
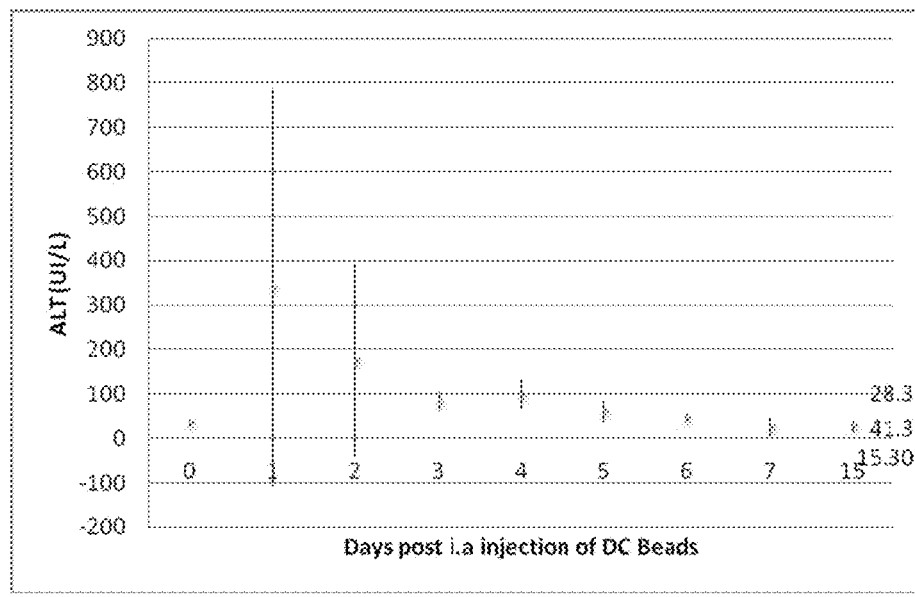
FIG. 13 Mean ALT level (UI/L) after intra arterial administration of 0.05 ml DC Beads in the arterial branch supplying the left lateral lobe of the liver (group 2).
Figure 14:
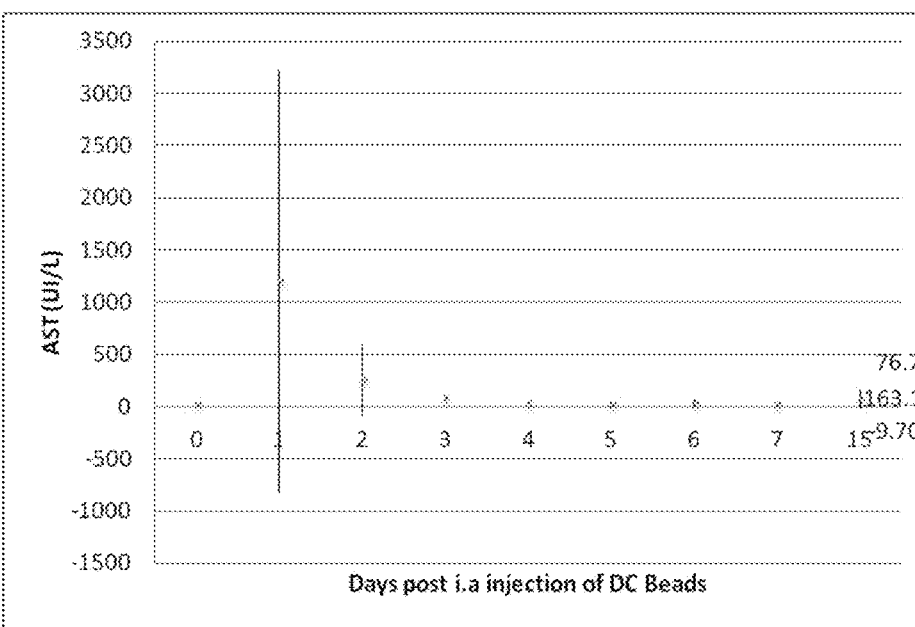
FIG. 14 Mean AST level (UI/L) after intra arterial administration of 0.05 ml DC Beads in the arterial branch supplying the left lateral lobe of the liver (group 2).
Figure 15:
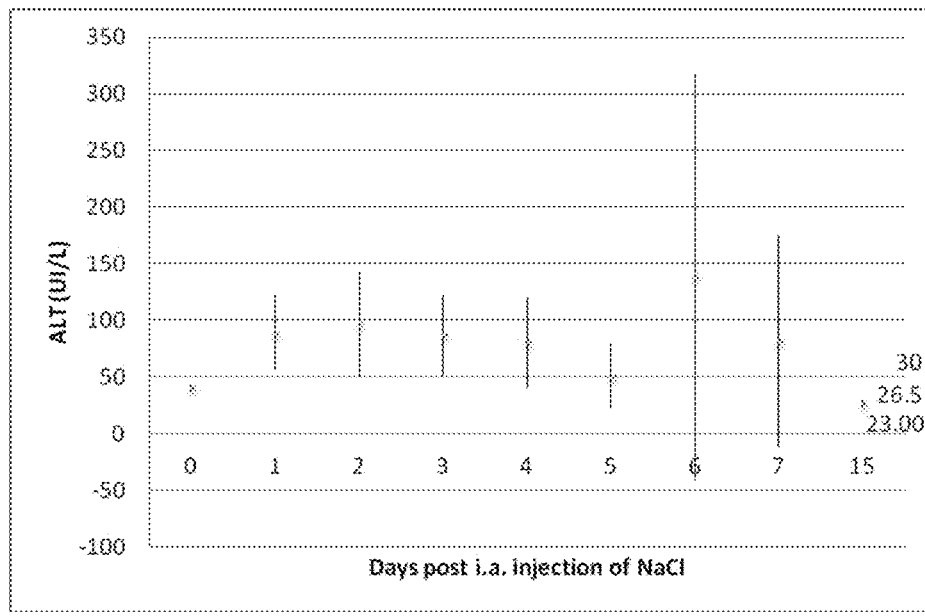
FIG. 15 Mean ALT level (UI/L) after intra arterial administration of 0.05 ml NaCl 0.9% in the arterial branch supplying the left lateral lobe of the liver (group 3).
Figure 16:
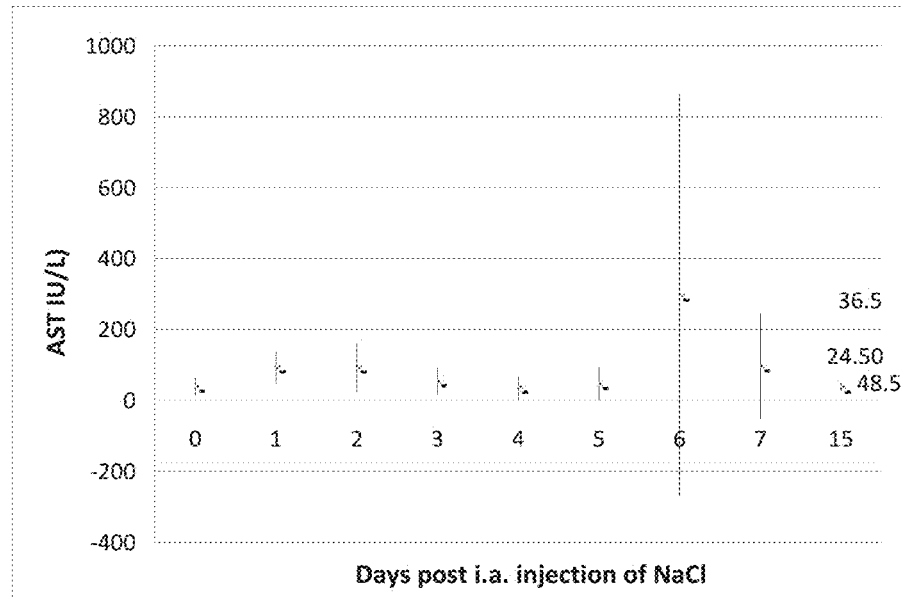
FIG. 16 Mean AST level (UI/L) after intra arterial administration of 0.05 ml NaCl 0.9% in the arterial branch supplying the left lateral lobe of the liver (group 3).
Figure 17:
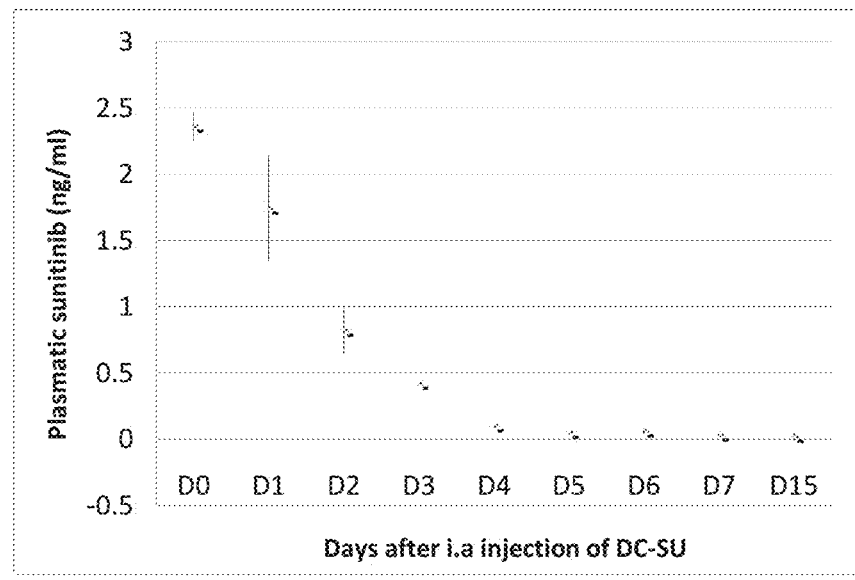
FIG. 17 Plasmatic sunitinib levels (ng/ml) after intra arterial administration of 0.05 ml DC Beads loaded with 1.5 mg of sunitinib in the common hepatic artery in 6 rabbits.
Figure 18:
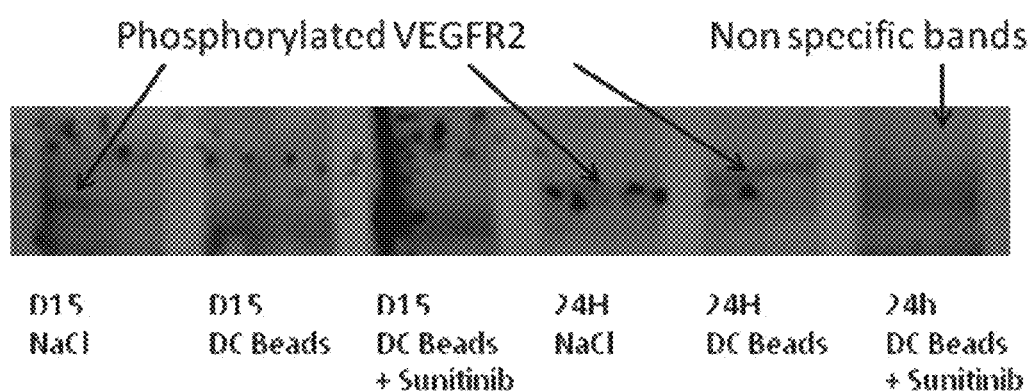
FIG. 18 Western blot analysis shows that embolization with DC Beads+sunitinib inhibits the activity of the RTKs and that embolisation with bland DC Beads increases RTK activity after 24 h.
Figure 19:
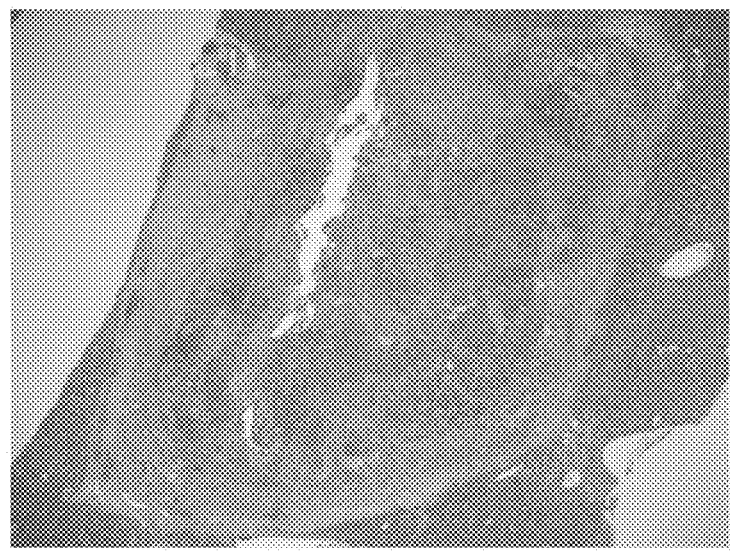
FIG. 19 Histopathological examination of tumor 15 days after embolization with DC Beads loaded with sunitinib. Aspect of necrotic tumor under light microscopy with HE staining. The tumor appears 100% necrotic.
Figure 20:
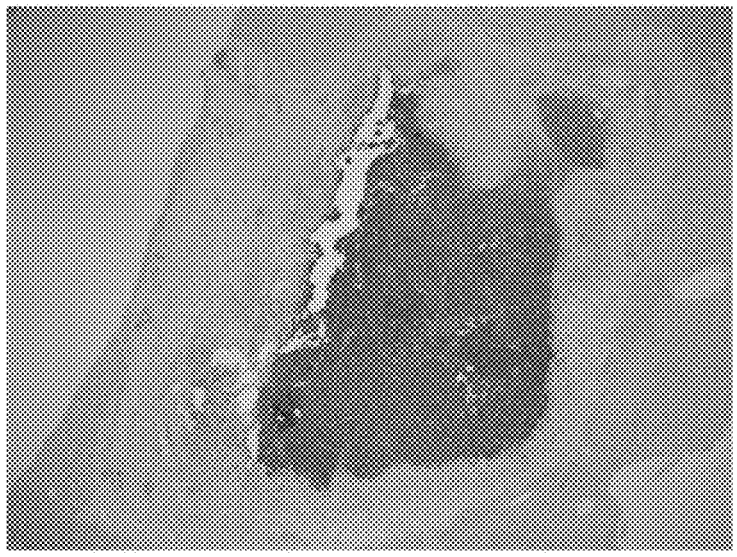
FIG. 20 Histopathological examination of tumor 15 days after embolization with DC Beads loaded with sunitinib. TUNEL staining confirms 100% necrosis FIG. 21 Histopathological examniation of tumor after embolization with DC Beads loaded with Sunitinib showing DC Beads located in the periphery of tumor and in portal spaces.
Figure 21:
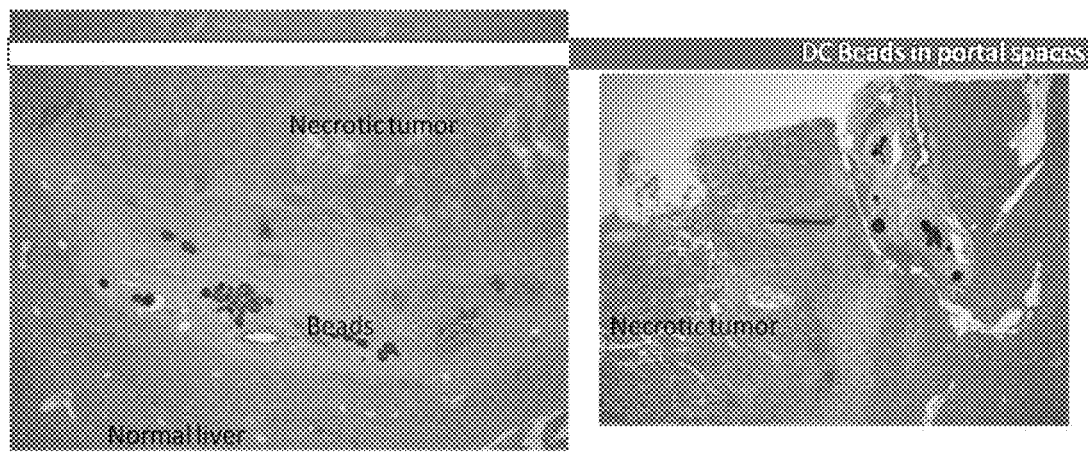

DCbead were loaded as described in Example 1. Release experiment were performed using the USP method 4 (flow-through), with a Sotax CE 6 apparatus, at 37° C., under constant flow (CY7 pump at 5 ml/min) in NaCl 0.9%, with n=6 cells in parallel. Spectrophotometric determination at 430 nm was used to measure drug concentration. The results are shown in FIG. 3, demonstrating a gradual release over 6 hours. The amount of drug eluted was a function of the total salt content of the receiving bath, as expected for a ion-exchange mechanism of delivery.

Example 4: Loading Sunitinib into Quadrasphere™

A vial of 25 mg of dry Quadraspheres™ 50-100 microns (Biosphere Medical) was used. To allow complete swelling of the beads, a sufficiently large volume (10 mL) of solution has to be used, prepared as follows: to 25 mg of sunitinib base was added 0.88 g of HCl 0.1 N, i.e. an 1.05 molar ratio to sunitinib. The vial was gently shaken until complete dissolution. Then a 5% w/w glucose solution was added to reach a final volume of 10 mL corresponding to a sunitinib concentration of 2.5 mg/mL. The 10 mL of sunitinib solution was then poured in the Quadrasphere™ vial containing 25 mg of dried microspheres.

Ten microliters of supernatant was withdrawn at predefined time points and absorbance measured at 430 nm. After 15 min, less than 1% of the drug could be found in the supernatant. After 2 hours, 99.6% of the drug could be loaded in the Quadrasphere. This demonstrates complete adsorption of the sunitinib by the Quadrasphere™ microspheres.

Example 5: Evaluation of the Pharmacokinetic and Toxic of Sunitinib Eluting Beads in the Rabbit Material and Methods
Animal Model.
Adult healhy male New Zealand White Rabbits (n=12) weighing between 3.2-2.8 kgs were used.

Preparation of Sunitinib Loaded DEB.

DC Beads measuring between 100-300 μm (Biocompatibles) were used. The maximum volume of DC beads that can be administered in the rabbit liver was estimated to approximately 0.2 ml, DC Beads were loaded at 30 mg of sunitinib/ml. The DC beads were loaded with sunitinib by suspension for 2 hours in a sunitinib solution to achieve the required concentration of sunitinib per ml of beads. Small aliquots of 0.2 ml containing 6 mg of sunitinib were prepared in individual seringes for embolization of the whole liver. The stability of the drug has been previously verified by HPLC analysis, in vitro studies showed that the loaded drug can be released within a few hours ($T_{75\%}$=1.3 hours) in a saline medium. The exact kinetics and extent of release depends on saline concentration and volume, as expected for a ionic exchange mechanism.

Experimental Protocol.

Animals were separated in 3 groups. The first two groups (groups 1 and 2, n=4 and 4 respectively) received 0.2 ml of DEB+sunitinib (6 mg) administered intra arterially in the hepatic artery. Four animals (group 1) were sacrificed 6 hours after embolization and 4 animals (group 2) were sacrificed 24 hours after embolization. The third group (group 3, n=4) received sunitinib per os at a unique dose of 6 mg, which should yield a therapeutic plasmatic concentration (Cmax) of 45-55 ng/mL according to previous pharmacological studies (*FDA drug online Sunitinib* p78). Two animals in group 3 were sacrificed a 6 hours and 2 at 24 hours.

Dosage of Liver Enzymes After Administration.

Liver enzymes were measured from blood samples obtained by a catheter placed in the vein of the rabbit's ear, immediately before embolization or oral administration of the drug and 6 hours. An additional blood sample was obtained at 24 hours for group 2 and those animals sacrificed at 24 hours in group 3.

Dosage of Sunitinib After Administration.

Plasmatic sunitinib level were measured immediately before and after the end of the embolization procedure as well as 1, 2, 3, 4, 5, 6 hour after administration. An additional blood sample was obtained at 24 hours for group 2 and those animals sacrificed at 24 hours in group 3. Whole blood samples were collected into EDTA-K tubes and centrifugated. Plasma samples were protected from light and stored frozen until analysis by LC MS/MS tandem mass spectrometry [16]. Determination of sunitinib concentration in the liver was performed using the same mass spectrometry method after sacrifice of the animals in the 3 groups.

Results

This study focused on the in vivo pharmacokinetics of sunitinib administered by means of DEB. Serial dosage of liver enzymes allowed to evaluate potential toxicity of this administration modality and plasmatic sunitinib levels after treatment allowed to evaluate the systemic passage of the drug which is expected to be minimal.

Liver Function Evaluation:

Administration of sunitinib/DC Beads caused a significant elevation of ALT, AST compatible with cytolysis as is usual after TACE in the liver. Bilirubin plasmatic levels were not affected by the treatment staying below the detection threshold in all measurements. Administration of sunitinib p.o. did not cause any alteration of liver enzymes Plasmatic Sunitinib Level:

After administration of DC Beads+sunitinib in the hepatic artery, plasmatic sunitinib remained <50 ng/ml (minimum concentration predicted from chemical- and cellular-based assays to inhibit VEGFR and PDGFR).

Sunitinib Level in the Hepatic Tissue:

Sunitinib levels in the liver tissue were performed 6 hours (n=1) and 24 hours (n=3) after aminitration of 2 ml DC Beads loaded with 6 mg of sunitinib in the common hepatic artery. Four samples were obtained from each liver to avoid differences due to inhomogeneous perfusion of the liver during the administration. The mean levels were 3870 ng/ml at 6 hours and 4741.7 ng/ml at 24 hours which is way above the minimum concentration predicted from chemical- and cellular-based assays to inhibit VEGFR and PDGFR.

Conclusion

The administration of sunitinib by means of loaded DC Beads directly injected in the hepatic artery did not elicit unexpected toxicity. Determination of sunitinib in the liver tissue after treatment showed that the drug is effectively eluted by the DC Beads in the tissues with obtention of high concentration in liver tissue. Serial plasmatic measurements showed a low release (infra therapeutic) in the systemic circulation.

Example 6: Evaluation of the Antitumoral Effect of Sunitinib Eluting Beads in a VX2 Rabbit Tumour Model Material and Method
Animal Model.

Adult male New Zealand White Rabbits (n=15) weighing between 3.0 and 3.8 kgs were used.

Experimental Protocol.

The tumors were implanted in the left liver lobe of the rabbits by laparotomy under general anesthesia according to the technique described by Lee et al [17]. Rabbits were separated in three groups: group 1 (n=7) received intra-arterial hepatic DEB+sunitinib, group 2 (n=6) received intra-arterial hepatic DEB without drug and group 3 (n=6) received a sham embolization with distilled water. Selective hepatic arteriography was performed 2 weeks after tumor implantation, under general anesthesia. The arterial anatomy, tumor staining, vascularity, size and location were first assessed by a common hepatic arteriography. Then subsequent catheterization of the tumor feeding vessel was performed and the treatment (DEB+sunitinib) was administered. One animal in each group was sacrificed at 24 hours and the other were kept alive untile the $15^{th}$ day.

Preparation of Sunitinib Loaded DEB.

The same DC Beads measuring between 100-300 μm (Biocompatibles) were used in this experiment. DC beads were loaded with sunitinib by suspension for 2 hours in a sunitinib solution to achieve a concentration of 30 mg/ml. Small aliquots of 0.05 ml of DC Beads containing 1.5 mg of sunitinib were prepared for supra selective embolization of the tumor.

Measurments of Plasmatic Liver Enzymes After Administration.

Liver enzymes were measured from blood samples obtained by a catheter placed in the vein of the rabbit's ear, immediately before and after administration, and every day until the $7^{th}$ day, One additional blood sample was obtained at the $15^{th}$ day in those animals still alive.

Measurment of Plasmatic Sunitinib Levels After Administration.

Blood samples were collected to determine circulating levels (i.e. "systemic exposure") of sunitinib. Samples were collected from a catheter placed in the vein of the rabbit's ear immediately before and after administration, and every day until the $7^{th}$ day. One additional blood sample was obtained at the $15^{th}$ day in those animals still alive. Whole blood samples were collected into EDTA-K tubes and centrifugated. Plasma was protected from light and stored frozen until analysis by a validated LC-MS/MS method. Toxicokinetic calculations were performed using the non-compartmental approach.

Anatomopathological Evaluation.

After sacrifice of the animals the livers were harvested. Sunitinib level in tumoral tissue were measured by LC MS/MS as in the pharmacokinetic study. The rest of the tumor was fixed in formaldehyde for histopathological preparation. The percentage of necrosis and MVD were estimated by histopathological analysis using the TUNEL method and CD-31 labelling. We evaluated VEGFR-2 phosphorylation by Western Blot analysis of tumor homogenates as an indirect read-out of VEGF activity.

Results

This study aimed to confirm the local antitumoral efficacy of sunitinib when administered intra-arterially by the means of DEB in VX2 carrying rabbits.

Catheterism of the arterial branch supplying the left lateral lobe of the liver and administration of the scheduled treatment was successful in all animals.

Survival:

In Group 1 no animal died during follow up. In group 2 and 3, 2 and 3 animals respectively died during follow-up. In group 2, one animal died on the $3^{rd}$ day from gastric perforation and one animal died on the $14^{th}$ day from respiratory insufficiency due to massive lung metastatisation. In group 3, one animal died on the $3^{rd}$ day from gastric perforation, one presented with paraplegia on the $7^{th}$ day probably due to a spine fracture during manipulation and was therefore sacrificed and one died on the $9^{th}$ day from respiratory insufficiency due to massive lung metastatisation. We did not observe any lung metastasis at necropsis in animals in group 1.

Liver Function:

In group 1, administration of sunitinib/DC Beads caused significant elevation of ALT, AST occuring around the $2^{nd}$ and 3rd day after treatment. Bilirubin plasmatic levels were not affected. PAL and LDH level did not seem to vary in a significant manner after treatment. In group 2, administration of DC Beads without sunitinib in the arterial branch supplying the left lateral lobe of the caused an elevation of both AST and ALT.Bilirubin plasmatic levels were not affected. PAL and LDH level did not seem to vary in a significant manner after treatment.

In group 3, administration NaCl in the arterial branch supplying the left lateral lobe of the liver in group 3 did not cause any significant effect of treatment on plasmatic liver enzymes levels.

Plasmatic Sunitinib Levels

In group 1, serial measurments of plasmatic sunitinib levels performed in group 1 showed that a peak in concentration occured immediately after i.a. administration followed by a slow derease until the 3rd-4th day.

Plasmatic concentration of sunitinib remained <50 ng/ml (minimum concentration predicted from chemical- and cellular-based assays to inhibit VEGFR and PDGFR).

Evaluation of RTK Phosphorylation by Western Blot:

In group 1, there was evident lack of phosphorylation of the RTK 24 hours after embolization with sunitinib loaded DEC Beads. In group 2 there was an augmentation of the RTK phosphorylation 24 hours after embolization with bland DC Beads. No significant difference was observed 15 days after treatment.

Histopathological Evaluation of antitumoral Effect:

On hisotpathological evaluation we observed that most of the tumors harvested at 15 days were in a large proportion necrotic. It was impossible to differentiate necrosis from the spontaneous evolution of the VX2 tumor model from necrosis induced by treatment. However interestingly we did not observe any case of distant metastasis in group 1 treated by sunitinib loaded beads Conclusion As in the previous study, the administration of sunitinib by means of loaded DC Beads directly injected in the branch of the hepatic artery supplying the tumor was well tolerated. This treatment seems to offer a survival advantage in VX2 carrying rabbits and interestingly no animal treated with DC Beads loaded with sunitinib presented distant metastasis at necropsy. We were able to demonstrate the inhibition of the RTK by western blot in tumors samples after embolization with DC Beads loaded with sunitinib as there was a rise of RTK activity in tumors treated by DC Beads without sunitinib. This finding supports the concept that embolization with particles loaded with an antiangiogenic agent could be useful in the treatment of various hyper vascularized tumors. Further studies are currently undercousre to further evaluate the antitumoral effect of this combination in animal and in vitro models.

Example 7: Feasibility of Imatinib Loading in DC Bead

Imatinib was solubilized at pH 4.5 using HCl diluted in a glucose 5% solution. The drug was used at a concentration of 0.5 mg per mL of solution. DCbead (sulfonated polyvinyl alcohol beads, 100-300 microns diameter, 1 mL) were suspended in 5 mL of this solution and left in contact for 2 hours. Elution in saline (NaCl 0.9%) was monitored by high pressure liquid chromatography (mobile phase: water/methanol/triethylamine 64/35/1 v/v/v, pH 4.8, UV detection at 268 nm). After 4 hours, approximately 40% of the drug amount present in the initial loading solution could be recovered in the elution medium, as indicated by the area under the HPLC peaks, showing the feasibility of loading imatinib into the hydrogel beads.

The invention claimed is:

1. A method for treating a solid tumor cancer in a patient comprising administering to said patient a therapeutically effective amount of a chemoembolization composition comprising anti-angiogenic agent and a sugar or poly-ol loaded in anionic drug eluting beads;
wherein said anionic drug eluting beads comprise a hydrophilic, water-insoluble, biocompatible polymeric material bearing negatively charged groups;
wherein said antiangiogenic agent is electrostatically bonded to the polymer;
wherein said anti-angiogenic agent is selected from the group consisting of sunitinib, angiostatin K1-3, arresten, DL-α-difluoromethyl-ornithine, fumagillin, genistein, staurosporine, (±)-thalidomide, tumstatin, axitinib, bortezomib, bosutinib gefitinib, pazopanib, semaxanib, sorafenib, vandetanib, vatalanib, canertinib, dovitinib, dasatinib, erlotinib, imatinib, lapatinib, masutinib, mubitinib, lestaurtinib, pazopanib, tandutinib and vismodegib.

2. The method of claim 1, wherein said anti-angiogenic agent is selected from the group consisting of sunitinib, angiostatin K1-3, arresten, DL-α-difluoromethyl-ornithine, genistein, staurosporine, (±)-thalidomide, tumstatin, axitinib, bortezomib, bosutinib gefitinib, pazopanib, semaxanib, sorafenib, vandetanib, vatalanib, canertinib, dovitinib, dasatinib, erlotinib, imatinib, lapatinib, masutinib, mubitinib, lestaurtinib, pazopanib, tandutinib, lestaurtinib, pazopanib, tandutinib and vismodegib.

3. The method of claim 1, wherein said anti-angiogenic agent is sunitinib.

4. The method of claim 1, wherein said anti-angiogenic agent is imatinib.

5. The method of claim 1, wherein said anti-angiogenic agent is vandetinib.

6. The method of claim 1, wherein said sugar or polyol is selected from the group consisting of glucose, sucrose, dextran, mannitol, sorbitol and trehalose.

7. The method of claim 1, wherein said sugar or poly-ol is glucose.

8. The method of claim 1, wherein said solid tumor cancer is a malignant hypervascularised tumor.

9. The method of claim 8, wherein said malignant hypervascularised tumor is selected from the group consisting of hepatocellular carcinoma (HCC), liver metastasis, cholangioma, neuroendorine tumor, GIST liver metastasis and renal cancer.

10. A method for treating a solid tumor cancer in a patient comprising administering to said patient a therapeutically effective amount of a chemoembolization composition comprising anti-angiogenic agent and a sugar or poly-ol loaded in anionic drug eluting beads;
wherein said anionic drug eluting beads comprise a hydrophilic, water-insoluble, biocompatible polymeric material, bearing negatively charged groups;
where said antiangiogenic agent is electrostatically bonded to the polymer,
wherein said anti-angiogenic agent is selected from the group consisting of sunitinib, angiostatin K1-3, arresten, DL-α-difluoromethyl-ornithine, fumagillin, genistein, staurosporine, (±)-thalidomide, tumstatin, axitinib, bortezomib, bosutinib gefitinib, pazopanib, semaxanib, sorafenib, vandetanib, vatalanib, canertinib, dovitinib, dasatinib, erlotinib, imatinib, lapatinib, masutinib, mubitinib, lestaurtinib, pazopanib, tandutinib and vismodegib;
wherein said anionic drug eluting beads comprise a sugar or poly-ol solution; and
wherein said chemoembolization composition does not comprise precipitated drug.

11. The method of claim 10, wherein said anti-angiogenic agent is selected from the group consisting of sunitinib, angiostatin K1-3, arresten, DL-α-difluoromethyl-ornithine, genistein, staurosporine, (±)-thalidomide, tumstatin, axitinib, bortezomib, bosutinib gefitinib, pazopanib, semaxanib, sorafenib, vandetanib, vatalanib, canertinib, dovitinib, dasatinib, erlotinib, imatinib, lapatinib, masutinib, lestaurtinib, pazopanib, tandutinib and vismodegib.

12. The method of claim 10, wherein said anti-angiogenic agent is sunitinib.

13. The method of claim 10, wherein said anti-angiogenic agent is imatinib.

14. The method of claim 10, wherein said antiangiogenic agent is vandetinib.

15. The Method of claim 10, wherein said sugar or polyol is selected from the group consisting of glucose, sucrose, dextran, mannitol, sorbitol and trehalose.

16. The method of claim 10, wherein said sugar or poly-ol is glucose.

17. The method of claim 10, wherein said solid tumor cancer is a malignant hypervascularised tumor.

18. The method of claim 17, wherein said malignant hypervascularised tumor s selected from the group consisting of hepatocellular carcinoma (HCC), liver metastasis, cholangioma, neuroendorine tumor, GIST liver metastasis and renal cancer.

19. A method for treating a solid tumor cancer in a patient comprising administering to said patient a therapeutically effective amount of a chemoembolization composition comprising an anti-angiogenic agent and a sugar or poly-ol loaded in anionic drug eluting beads;
  wherein said anionic drug eluting beads comprise a hydrophilic, water-insoluble, biocompatible polymeric material, bearing negatively charged groups;
  wherein said antiangiogenic agent is electrostatically bonded to the polymer;
  wherein said anti-angiogenic agent is selected from the group consisting of sunitinib, angiostatin K1-3, arresten, DL-α-difluoromethyl-ornithine, fumagillin, genistein, staurosporine, (±)-thalidomide, tumstatin, axitinib, bortezomib, bosutinib gefitinib, pazopanib, semaxanib, sorafenib, vandetanib, vatalanib, canertinib, dovitinib, dasatinib, erlotinib, imatinib, lapatinib, masutinib, mubitinib, lestaurtinib, pazopanib, tandutinib and vismodegib;
  wherein said anionic drug eluting beads comprise a sugar or poly-ol solution; and
  wherein said anionic drug eluting beads do not comprise precipitated drug.

20. The method of claim 19, wherein said anti-angiogenic agent is selected from the group consisting of sunitinib, angiostatin K1-3 arresten, DL-α-difluoromethyl-ornithine, genistein, staurosporine, (±)-thalidomide, tumstatin, axitinib, bortezomib, bosutinib gefitinib, pazopanib, semaxanib, sorafenib, vandetanib, vatalanib, canertinib, dovitinib, dasatinib, erlotinib, imatinib, lapatinib, masutinib, mubitinib, lestaurtinib, pazopanib, tandutinib and vismodegib.

21. The method of claim 19, wherein said anti-angiogenic agent is sunitinib.

22. The method of claim 19, wherein said anti-angiogenic agent is imatinib.

23. The method of claim 19, wherein said anti-angiogenic agent is vandetinib.

24. The Method of claim 19, wherein said sugar or polyol is selected from the group consisting of glucose, sucrose, dextran, mannitol, sorbitol and trehalose.

25. The method of claim 19, wherein said sugar or poly-ol is glucose.

26. The method of claim 19, wherein said solid tumor cancer is a malignant hypervascularised tumor.

27. The method of claim 25, wherein said malignant hypervascularised tumor is selected from the group consisting of hepatocellular carcinoma (HCC), liver metastasis, cholangioma, nouroendorine tumor, GIST liver metastasis and renal cancer.

28. The method according to claim 1, wherein said hydrophilic, water-insoluble, biocompatible polymeric material is a modified polyvinyl alcohol or acrylic co-polymer.

29. The method according to claim 1, wherein said hydrophilic water-insoluble, biocompatible polymeric material is selected from sulphonate-modified polyvinyl alcohol hydrogel and carboxyl-modified polyvinyl alcohol-co-sodium acrylate.

30. The method according to claim 10, wherein said hydrophilic, water-insoluble, biocompatible polymeric material is a modified polyvinyl alcohol or acrylic co-polymer.

31. The method according to claim 10, wherein said hydrophilic, water-insoluble biocompatible polymeric material is selected from sulphonate-modified polyvinyl alcohol hydrogel and carboxyl-modified polyvinyl alcohol-co-sodium acrylate.

32. The method according to claim 19, wherein said hydrophilic, water-insoluble, biocompatible polymeric material is a modified polyvinyl alcohol or acrylic co-polymer.

33. The method according to claim 19, wherein said hydrophilic water-insoluble, biocompatible polymeric material is selected from sulphonate-modified polyvinyl alcohol hydrogel and carboxyl-modified polyvinyl alcohol-co-sodium acrylate.

* * * * *